US006566853B2

(12) United States Patent
Li et al.

(10) Patent No.: US 6,566,853 B2
(45) Date of Patent: May 20, 2003

(54) MOLTEN METAL INCLUSION SENSOR PROBES

(75) Inventors: Mei Li, Dearborn, MI (US); Roderick I. L. Guthrie, Montreal (CA)

(73) Assignee: Limca Research Inc., Montreal (CA)

( * ) Notice: Subject to any disclaimer, the term of this patent is extended or adjusted under 35 U.S.C. 154(b) by 126 days.

(21) Appl. No.: 09/817,291

(22) Filed: Mar. 27, 2001

(65) Prior Publication Data

US 2001/0035747 A1 Nov. 1, 2001

(30) Foreign Application Priority Data

Mar. 27, 2000 (CA) ............................................. 2302121

(51) Int. Cl.[7] .................... G01N 27/00; B22D 46/00; G01R 27/08
(52) U.S. Cl. .................... 324/71.4; 324/71.1; 324/717; 324/724; 164/4.1
(58) Field of Search .............................. 324/71.1, 71.4, 324/717, 724; 164/4.1

(56) References Cited

U.S. PATENT DOCUMENTS

| 4,926,114 A | 5/1990 | Doutre ...................... 324/71.4 |
| 5,241,262 A | 8/1993 | Guthrie et al. ............. 324/71.1 |
| 5,834,928 A | 11/1998 | Doutre ...................... 342/71.4 |

FOREIGN PATENT DOCUMENTS

EP 0 682 241 A1 11/1995 .......... G01N/15/12

OTHER PUBLICATIONS

Mei Li and Roderick R.L. Guthrie—Numerical Studies of the Motion of particles in Current–Carrying Liquid Metals flowing in a Circular Pipe—pp. 357–364, vol. 31B, Apr. 2000 of Metallurgical and Materials Transactions B. Copy enclosed.

Primary Examiner—N. Le
Assistant Examiner—Donald M Lair
(74) Attorney, Agent, or Firm—Stanley J. Rogers

(57) ABSTRACT

Molten metal inclusion sensor probes have a sensing passage through which the molten metal passes, while direct current passes through the passage between two electrodes. The passage of an inclusion through the passage changes the resistance in the path, resulting in a pulse indicating its size, and enabling the number of particles in a sample to be counted. Previously the passage has been cylindrical, with or without a conical entrance, or of randomly smoothed profile produced by melting the probe material. High levels of background noise make pulse detection difficult, and operation is improved by the passage decreasing smoothly in cross-section in the flow direction, preferably with a parabolic or elliptical profile, and preferably with the exit of the same profile. The wall surface is formed to a smoothness of better than 1.016 micrometers (40 microinches), preferably 0.254 micrometers (10 microinches), permitting predetermination of the optimum testing and conditioning currents required.

18 Claims, 6 Drawing Sheets

Contour values:
A 2.19 x 10⁻³
B 6.56 x 10⁻³
C 1.09 x 10⁻²
D 1.53 x 10⁻²
E 1.97 x 10⁻²
F 2.40 x 10⁻²
G 2.84 x 10⁻²
H 3.28 x 10⁻²
I 3.72 x 10⁻²
J 4.15 x 10⁻²
K 4.59 x 10⁻²
L 5.03 x 10⁻²

ELECTRIC POTENTIAL DISTRIBUTION

ELECTRIC CURRENT DENSITY

MAGNETIC FLUX DENSITY

Contour values:
A -7.54 x 10⁻⁸
B -6.88 x 10⁻⁸
C -6.23 x 10⁻⁸
D -5.57 x 10⁻⁸
E -4.92 x 10⁻⁸
F -4.26 x 10⁻⁸
G -3.61 x 10⁻⁸
H -2.95 x 10⁻⁸
I -2.29 x 10⁻⁸
J -1.64 x 10⁻⁸
K -9.83 x 10⁻⁹
L -3.28 x 10⁻⁹

ELECTROMAGNETIC FORCE

FLOW VELOCITY VECTORS

Radial velocity

R   S   T

FLOW WITH CONDITIONING CURRENT

MOLTEN METAL INCLUSION SENSOR PROBES

FIELD OF THE INVENTION

This invention is concerned with improvements in or relating to molten metal inclusion sensor probes, namely sensor probes that are used in apparatus for detecting the number, size and size distribution of inclusions in molten metal, the apparatus employing what is now known as the ESZ (Electric Sensing Zone) method. The invention is also concerned with improvements in or relating to methods of making molten metal inclusion sensor probes. Such sensor probes are used in the quality control of liquid metals, such as aluminium, magnesium and steel, and are particularly valuable for this purpose in that they permit rapid on-line monitoring of flowing molten metal.

REVIEW OF THE FIELD

The production and refining of metals from their ores inevitably results in what, for convenience in reference, are called herein "inclusions", such as precipitated secondary phase particles, drops of slag and gas bubbles, all of which have a more or less deleterious effect upon the technical properties of the metals. An even greater quantity and variety of inclusions may be found when scrap metal is being recycled and refined, either alone or as an addition to virgin metal, owing to the presence of various products of oxidation and corrosion, dirt, oils, paint, etc, on the scrapped articles. The presence of such inclusions within the resultant rolled or cast products is generally undesirable from the point of view of properties such as fatigue life, toughness, corrosion, tearing, splitting, surface quality, pinholes, etc., particularly when larger inclusions (e.g., dimensions>15 microns) are present. For example, the production of aluminium beverage can bodies is very sensitive to the presence of any inclusions within the can walls, whose thickness is of the order of 80 microns; large inclusions, which can be as large as 60 microns, can cause the metal to tear during deep drawing, or the can to perforate when its content is pressurized. Other applications in which cleanliness is critical are the production of thin sheets and lithographic plates. It is therefore essential to know whether or not the metal is sufficiently "clean" for its intended purpose, and also to show whether or not the refining processes employed are producing sufficiently clean metal.

A quantitative measurement method and apparatus for such inclusions, particularly in molten aluminium, that can be operated on-line has now become well established in the aluminium industry, and is known as the LiMCA system (Trademark of Limca Research Inc.); these are described and claimed for example in U.S. Pat. Nos. 4,555,662, 4,600,880, and 4,763,065, the disclosures of which are incorporated herein by this reference. Commercial equipment is manufactured under license by Bomem, Quebec City, Quebec, Canada. The application of the method and apparatus to the detection of inclusions during the refining and recycling of other metals is under development.

The ESZ method was used prior to its application to molten metals to measure inclusions in aqueous solutions in what was known as the Coulter counter, and relies upon the fact that any inclusion usually is of different conductivity (usually much lower) than the highly electrically conductive liquid metal in which it is entrained. A measured volume of the molten metal is passed through a sensing zone consisting of an orifice of specific size (usually 300 microns diameter for aluminium) in the wall or bottom of a tube of an electrically insulating material, usually be connecting a vacuum to the tube interior, while a constant current is maintained through the sensing zone between two electrodes disposed on opposite sides of the orifice. As an inclusion particle passes through the orifice the electrical resistance of the current path through the orifice changes in proportion to the volume of the inclusion, and this change is detected as a voltage pulse between the two electrodes, or more usually between two other electrodes in the current path provided for this purpose. The amplitude of each pulse indicates the size of the respective inclusion, while the number of pulses indicates the number of inclusions in the sample volume. Besides monitoring the quality of liquid metals in terms of the number and size distribution of lower conductivity inclusions, the LiMCA system can also be used for the detection and analysis of titanium diboride ($TiB_2$) particles that have been added to aluminium silicon casting alloys as grain refining agents. Titanium diboride is more conductive electrically than molten aluminium and voltage pulses of opposite polarity were observed.

Currently used on-line sensing probes for testing aluminium employ a sampling tube of electrically-insulating, heat-resistant material that is lowered into the metal, the tube forming a chamber into which the molten metal is sucked through a sensing zone orifice in or near to its lower end. The usual method employed at this time for forming the orifice is to drill a hole of suitable diameter through the wall of the tube, and then to heat the inlet opening using an intense micro-flame of sufficient temperature to melt the material, whereupon it flows to form a rounded edge under the action of the surface energy force that becomes operative. The current-supplying electrodes and/or the sensing electrodes may take the form of two rods disposed one inside and one outside the tube, or concentric tubes of a suitable conductive material applied to the inner and outer walls of the tube. In order for the ESZ method to operate successfully it is necessary that the electrical current path pass entirely through the electric sensing zone, and there should be no unwanted leakage between the liquid metal inside and that outside the sampling tube.

Since every particle registers a pulse when passing through the ESZ, and nonconductive particles of the same size but of different type, e.g. different density, give rise to voltage pulses of the same magnitude, it was initially impossible to discriminate between different types of inclusions within a melt. In the aluminium industry proprietary degassing units generate microbubbles and microdroplets of salt in the molten aluminium. These microbubbles and microdroplets interfere with the LiMCA probe and cause inaccuracies in its inclusion counts. In practice, microbubbles are relatively harmless compared to hard solid inclusions, and one therefore needs to distinguish one from the other from the metal quality control point of view. Better particle discrimination can be obtained by the application of DSP technology (Digital Signal Processing), which permits more information to be extracted from the signals by consideration of other parameters besides pulse height. Using the McGill DSP system each pulse can also be characterized by six other pulse parameters, namely start slope, end slope, time to maximum voltage, total signal duration, start time and end time.

Very early on the successful continuous in-line operation of the LiMCA system was found to depend on a procedure termed "conditioning", which involves passing an electric current of 200–300 amperes, compared to the sensing current of about 60 amperes, through the orifice for about 300 ms before taking a new sample when it is observed that the inflow rate of the molten metal has decreased, or when instabilities are observed in the voltage baseline. The application of this high current usually is found to correct these problems, it is presumed by removing particles that have stuck to the orifice walls and are obstructing the flow of the molten aluminium and other particles through the orifice. The mechanism for this conditioning effect is a key to LiMCA's successful implementation in melts of aluminium, and probably also in melts of other metals, but still needs be clarified. It is believed that the main mechanism has been identified and that the new sensing probe structures now provided and methods for their production renders its implementation even more effective than hitherto.

DEFINITION OF THE INVENTION

It is the principal object of the present invention to provide inclusion sensor probes for molten metals of new construction It is another principal object of the present invention to provide new methods of making inclusion sensor probes for molten metals.

It is a further principal object to provide such probes, and methods of making such probes, with sensing orifices of improved profile which facilitates the monitoring of the particles passing in the sensing zone, and also permits prior determination of the conditioning current that is required consisting of a short pulse of high current passed through the sensing zone.

In accordance with the present invention there is provided a molten metal inclusion sensor probe of the type which is immersed in the molten metal and detects inclusions therein by the electric sensing zone method, the probe comprising a sensor probe body of electrically insulating heat resistant material having in at least a part of a wall thereof a sensing passage for the flow of molten metal from one side of the body to the other, the sensing passage providing therein an electric sensing zone and extending about a longitudinal axis;

wherein the sensing passage decreases progressively in flow cross section area from its entrance to the electric sensing zone; and wherein the profile of the sensing passage from its entrance to the electric sensing zone is selected from, a parabola having the parabola determinant coincident with the sensing passage longitudinal axis and the focus within the sensor probe body and spaced from the sensing passage, and a segment of an ellipse having one axis parallel with the sensing passage longitudinal axis and within the body and an extension of its other axis passing through the electric sensing zone.

Also in accordance with the invention there is provided a method of making a molten metal inclusion sensor probe as specified in the immediately preceding paragraph, the method including the step of forming the sensing passage in the wall to the specified profile by an operation that will provide a passage wall smoothness of predetermined value.

Further in accordance with the invention there is provided a molten metal inclusion sensor probe of the type which is immersed in the molten metal and detects inclusions therein by the electric sensing zone method, the probe comprising a sensor probe body of electrically insulating heat resistant material having in at least a part of a wall thereof a sensing passage for the flow of molten metal from one side of the body to the other, the sensing passage providing therein an electric sensing zone and extending about a longitudinal axis;

wherein the sensing passage decreases progressively in flow cross section area from its entrance to the electric sensing zone; and wherein the passage has been produced by a machining operation to have a wall surface smoothness of better than 1.016 micrometers (40 microinches).

DESCRIPTION OF THE DRAWINGS

Molten metal inclusion sensor probes, and methods for the production of sensing passages therein, which are preferred embodiments of the invention, will now be described by way of example with reference to the accompanying diagrammatic drawings, wherein.

DESCRIPTION OF THE PREFERRED EMBODIMENTS

Figure 1:
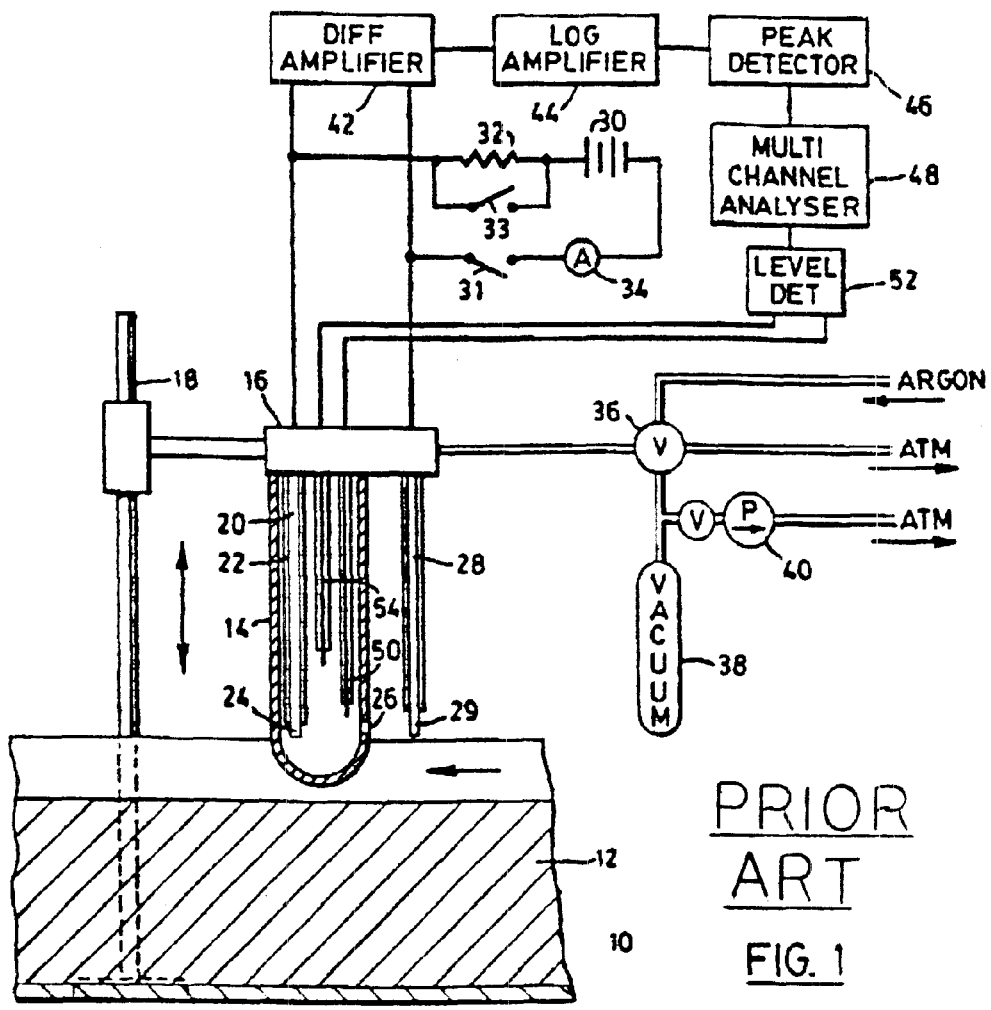
FIG. 1 is a schematic representation of prior art apparatus employing the LiMCA system for the measurement of inclusions in aluminium.

A prior art apparatus employing the LiMCA system is illustrated very schematically in FIG. 1. For example, a trough 10 conveys the molten metal 12 to be tested from the furnace in which it has been melted to subsequent treatment stages such as a degasser, filter bed and caster. The cleanliness of the molten metal, either in the flowing stream, or in a stationary test vessel (not illustrated), can be examined immediately and on line by drawing a sample, usually by means of reduced pressure, into a sample receiving test container 14, usually an elongated replaceable tube, which is closed at its lower end, and is removably mounted via its open upper end in an end cap 16. The cap is mounted for vertical up and down movement so that the tube can be dipped at will into the flowing stream 12 and withdrawn therefrom, the mounting means for this being shown diagrammatically herein as a standard 18. The end cap has four electrodes protruding downwardly therefrom, three of which enter the tube interior while the fourth is outside. One of the three internal electrodes is a current-carrying electrode 20 consisting of a metal rod, the upper part of which is encased in a heat insulating material 22, so that only the exposed lower tip 24 immediately adjacent to a sensing passage 26 in the container wall will be in electrical contact with molten metal that enters the container. The outer electrode 28 is also a current-carrying electrode and is mounted by the end cap 16 so as to extend parallel to the first electrode 20 with its bare lower tip 29 also immediately adjacent to the passage 26. The resultant current path between the electrodes 20 and 28 and through the sensing passage 26 is supplied with current from a battery 30 via a ballast resistor 32 that can be shunted when required by a switch 33 to increase the current flow to a "conditioning" value. One of the battery leads includes an on/off switch 31 and an ammeter 34. The end cap 16 also provides a fluid connection from the interior of the test container to a three-way valve 36, which permits the interior to be connected alternatively to a source of reduced pressure, or to a source of a suitable shielding inert gas, such as argon, or to the atmosphere. The reduced pressure source consists of a reservoir 38 which is exhausted as required in between tests through valve 36 by a pump 40. The two electrodes 20 and 28 are connected to a differential amplifier 42 and thence to a logarithmic amplifier 44, a peak detector 46 and multichannel analyser 48, which can also serve as a recorder.

Before use the interior of the container 14 is flushed with a gas such as argon or nitrogen and the container is then lowered into the metal 12. The valve 36 is then operated to connect the container interior to the reduced pressure reservoir, whereupon the molten metal is drawn smoothly and rapidly through the passage 26. As soon as enough metal has entered the container to touch and immerse the tip 24 of the electrode 20 a current path is established between the two electrodes 20 and 28 and through the passage. The analyser/recorder 48 is switched on when sufficient metal has entered the container to contact the lower level electrode 50 of a metal level detector 52, and is switched off when the metal contacts an upper level detection electrode 54. Since the area of contact between the liquid metal 12 and the electrodes 20 and 28 is limited to the tips 24 and 29, the only changes in voltage that are measured are those arising from the displacement of metal by inclusions passing through the sensing passage 26. Each of these inclusions when sensed produces a voltage pulse above or below the steady state value. Thus, as each particle passes through the passage 26 it displaces its own volume of the liquid metal and causes a change in the electrical resistance between electrodes 20 and 28, the magnitude of the pulse being related to the ratio between the cross section flow area of the passage and the size of the particle by a known relation. The voltage pulses are of relatively low amplitude superimposed on a large D.C signal and these are fed to the differential pre-amplifier 42 and filtered to remove the large D.C. component and inevitable high frequency noise. The accurate and reliable detection and measurement of these pulses among the high level noise is very difficult and limits the size of inclusion that can positively be detected to about 15–20 micrometers. The logarithmic amplifier 44 extends the dynamic range of the signal, and its output is fed to the peak detector which samples the signal and produces discrete pulses of fixed length that can be handled by the analyser 48. The analyser counts the number of these pulses and also analyses them as to size. The output of the analyser is therefore a histogram of particle number from which the particle concentration and particle size distribution in the specimen can be determined.

Figure 2:
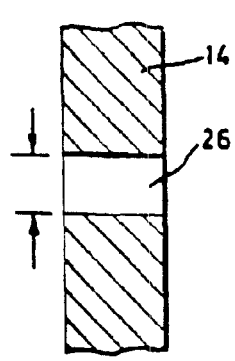
FIGS. 2–4 are longitudinal cross-sections through the lower part of a prior art sampling tube container as used in the apparatus of FIG. 2 to show different prior art profiles of the electric sensing zone sampling passage.
Figure 3:
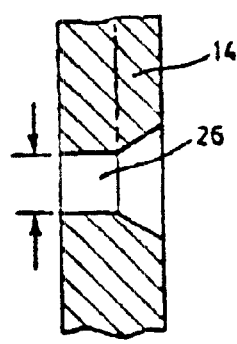
Figure 4:
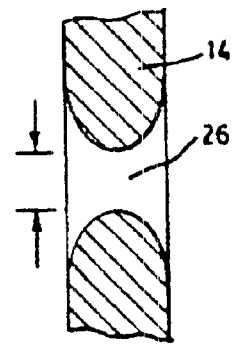

The suggested range of sensing passage diameters is 100 to 5000 micrometers, more usually for the lower melting point metals such as aluminium and magnesium of 200 to 500 micrometers, the value chosen depending primarily on the size of the inclusions in the melt and of typical inclusions to be measured. For sampling in aluminium the container 14 typically is a tube of a refractory material, for example a boro-silicate glass with a wall thickness of 1 mm to give a bore 26 of the same length. When used to sample aluminium the sensing passage is of diameter about 300 micrometers. FIG. 2 shows one form taken by the passage in a prior art apparatus, e.g. for testing molten steel, consisting of a drilled hole of uniform diameter along its length. FIG. 3 shows another version in which the entrance to the drilled hole of FIG. 2 has been enlarged by drilling a conical entrance portion extending into the passage, in order to give a more laminar flow into and through the passage. FIG. 4 shows the type of passage usually employed in a sensor probe for aluminium, where the tube is of a material that can readily be softened by heating. Thus, a flame is applied to a cylindrical hole as shown in FIG. 2 of sufficient temperature and heat capacity to melt the material around the hole, so that the material flows under the action of surface energy until its edges, particularly the circular entry edge, are converted to more or less smoothly randomly rounded respective profiles. The part of the passage of smallest diameter, or equivalent diameter if it is not truly circular, due for example to irregularity in the melting, constitutes the sensing zone proper. The diameter of the sensing zone can easily be measured by a gauge rod inserted into the passage, but the sensing passage profile obtained will vary in dependence upon the material from which the tube is made and the specific heating conditions, including the skill of the fabricator, under which each passage has been formed, there being no guarantee that the wall is truly smooth and uniform about the flow axis. Examination of the orifices of commercial versions of such tubes shows that their shapes are somewhat irregular, and attempts to develop a mathematical term for use in analysis of flow through such orifices has required, as a practical compromise, the fitting of at least a second order polynomial to the observed shape. Since it was found in practice that such rounding did enable relatively stable signals to be obtained, it appears that this was then deemed to be all that was required. The effective cross section area should be as small as possible, so that the passage of the smaller inclusions will produce clearly detectable pulses, but cannot be too small, since it is then found that inflow rates quickly decrease and the voltage baseline quickly becomes unstable. It is believed that the cause of this instability etc. is most likely that the inclusions of non-conducting material are directed toward the passage wall by the electromagnetic force generated therein, as will be described in more detail below, and may be sticking to the wall, reducing and disrupting the desired smooth laminar flow of the metal through the passage. A large inclusion may of course be unable to pass through and almost block the bore. A gradual deterioration in accuracy of the testing, and instability of the baseline readings, from test to test, and even during a test, was found from the start of the LiMCA system. Fortunately it was also found early on that it was possible to restore the apparatus virtually to its original accuracy and stability before a test by the "conditioning" process as described above, which is presumed to operate by removing any such obstructions. The mechanism by which this occurs has not been known for certain.

One proposal that has been made to alleviate this problem is contained in U.S. Pat. No. 5,834,928 to Doutre, the disclosure of which is incorporated herein by this reference, whereby the metal is conveyed through a wider passage upstream of the sensing passage immediately before discharging into the sensing passage, this wider passage being defined by an electrically non-conductive surface positioned in the current path and providing a flow region having a constant hydrodynamic diameter of between 2 and 10 times that of the sensing passage. The invention depends upon the fact that since the inclusions are particles of conductivity different from the molten metal they are subjected to a self-induced magnetic flux and resultant electromagnetic force. When the particles are of lower conductivity (the usual situation) this electromagnetic force urges them radially outward away from the flow axis, while particles of higher conductivity are urged toward the flow axis. The provision of such an initial wider passage has the effect of removing substantially all liquid and gaseous inclusions from the molten metal before it passes through the sensing passage; generally such liquid and gaseous inclusions do not deleteriously affect the metal quality as much as the solid inclusions. The initial passage should also trap larger particles and prevent them from entering the sensing passage, so that a sampling tube with a smaller orifice can be used to more accurately detect the smaller inclusions, while a sampling tube with a larger orifice and without the initial passage can be used in another test to measure the larger inclusions A detailed mathematical discussion of the motions of particles entrained in a flow of liquid metal while subjected to a co-current flow of electric current is the subject of a paper entitled "Numerical Studies of the Motion of particles in Current-Carrying Liquid Metals Flowing in a Circular Pipe" by the inventors herein Mei LI and Roderick R. L. GUTHRIE, published in Pages 357–364, Volume 31B, April 2000 of Metallurgical and Materials Transactions B, the disclosure of which is incorporated herein by this reference, and to which reference may be made. The following non-mathematical discussion of these motions is believed to be sufficient to enable a person skilled in the art to understand and apply the teachings of the present invention, and reference can be made to the paper above if a more detailed mathematical explanation is required.

Because of the inherent difficulty of accurate detection and measurement of the small signal pulses generated by the passage of an inclusion through the sensing zone against the relatively large steady D.C. signal needed for successful operation, great care has had to be taken in the design of the accompanying equipment to try to reduce the background "noise" as much as possible. For example, a pre-evacuated vacuum reservoir 38 is provided, so that the pump can be turned off during the test and not cause electrical interference as it operates. For the same reason the battery 30 is rechargeable, instead of using an on-line D.C. supply from an A.C. source. Great care is taken in the design of the electronic circuits to provide as much electronic smoothing as possible and to reduce to the minimum any ground loops that are otherwise a major source of noise.

As will be demonstrated in more detail below, and as is well known, for example from the Doutre patent referred to above, inherently the sensing passage itself constitutes an electromagnetic circuit element. Thus, the metal under test is a highly conductive "wire" moving through the sensing passage in an intense electric field and consequently generates a correspondingly relatively high magnetic flux and resultant strong electromagnetic force which mechanically affects the particles and the flow within the electric sensing zone. Unless therefore the utmost care is taken to ensure that the rapid flow of the molten metal through the very narrow sensing passage is as smooth as possible the sensing passage itself can be a generator of deleterious background noise. It is believed that such noise may be generated for example as a result of vortices and fluctuations in the flow generated as a result of the action of the electromagnetic field on the fluid flow within the ESZ, the passage profile and the surface conditions of the passage wall, any such vortex and fluctuation potentially constituting a minuscule but potent electrodynamic noise generator. It will be noted that the flow rates of the molten metal are relatively high, e.g. 2–5 m/s, as is desired for satisfactory operation of the system, and these high rates are at values at which the flow can easily become turbulent, at which point useful readings can no longer be obtained. It is known for example that a stirred fluid contains vortices of size determined by the viscosity and temperature of the fluid, and such vortices can be of size the order of that of the particles to be detected, i.e. about 15–50 micrometers.

It is believed therefore that previous suggestions simply to make the entry to the sensing passage "smooth" to obtain a "smooth" flow are inadequate, and instead at least the entry portion of the sensing passage wall, and preferably also the exit portion thereof, must be shaped to a precise progressive profile selected either as parabolic or elliptical, so that a flow that is as laminar as possible is achieved with the possibility of the generation of fluctuations and internal vortices minimized. With the high rates of flow employed the stagnant boundary layers that normally are present with slower flowing columns of fluids are vanishingly thin, and owing also to the operating temperatures involved, there is relatively high wear by abrasion of the passage wall that increases the size of the passage until the tube becomes unusable. It is also believed therefore that the initial smoothness of the passage wall is also unexpectedly important, and even the standard roughness of a so-called "smooth" wall, as previously employed, may be sufficient to generate fluctuations and vortices contributing to the background noise as the metal passes over it. To this end a preferred method of producing the sensing passage 26 is to first drill a pilot hole of appropriate diameter and then enlarge the hole to the required maximum starting diameter, while at the same time producing a sufficiently precisely formed parabolic or elliptical profile. This can be done, for example, by use of a rotary grinding tool 84 of complementary profile which is fed into the pilot hole first from one side and then from the other, the grinding produced by the tool being supplemented, if necessary, by a finishing operation with a similarly profiled lapping tool. Thus, a standard surface finish for high quality machining is about 1.016 micrometers (40 microinches), but this is believed to be insufficient in that microscopic inspection of such a finished surface will reveal ridges and protrusions that are potential generators of noise-inducing fluctuations and vortices, and it is preferred instead to achieve surface finishes of better than 0.254 micrometers (10 microinches), and more preferably 0.127 micrometers (5 microinches). Such finishes are relatively readily attainable with currently available grinding and lapping tools. It is believed that the matter of an ultra-smooth surface for the sensing passage wall is of sufficient importance to be applicable also to any other profiles that are not necessarily parabolic or elliptical and to the "smooth" randomly curved surfaces that have been proposed hitherto. Since the surfaces are most conveniently produced by use of a precisely formed rotary tool they will inherently be symmetrical about the flow axis, and the most likely alternative profile is a semi-circular one, even though it not expected to be as efficient in the suppression of noise as parabolic and elliptical surfaces.

The curvature of a parabolic curve can be expressed as a coefficient of the polynomial:

$$Y = Ax^2 + R$$

where A is the coefficient and R is the radius at the sensing zone throat. When A is zero the passage is cylindrical, while when it is very large the throat becomes a knife edge; a preferred range of values for the coefficient is from 1.0 to 5.0, more preferably from 2.0 to 4.0. The value for the curves in the discussion below is 2.15.

Similarly, the curvature of an elliptical curve can be expressed as a coefficient $\lambda = b/a$ of its respective polynomial:

$$(X/a)^2 + (y/b)^2 = 1$$

where a and b are the half axes lengths respectively in the x and y directions. A preferred range of values for the coefficient $\lambda$ is from 0.2 to 2.5, more preferably from 0.5 to 2.0. The specific value employed for the curve evaluated is 0.5.

Figure 5:
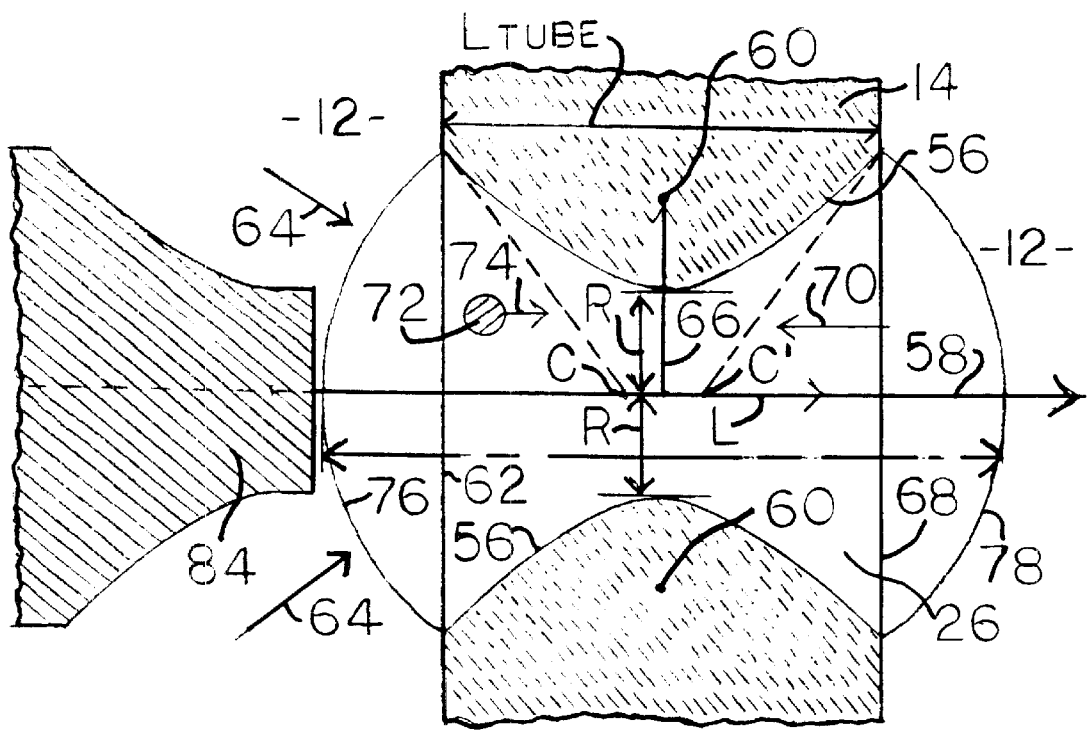
FIG. 5 shows to an enlarged scale a sensing passage in the side wall of a sampling tube wherein in accordance with the invention the sensing passage has a parabolic profile.

FIG. 5 shows to an enlarged scale the portion of the wall of the sensing container 14 that includes the sensing passage 26 and, in accordance with this invention this has a parabolic profile, the coefficient in this embodiment being of the preferred value 2.15, the directrix of the parabola being coincident with central longitudinal flow axis 58, about which the parabola is rotated to generate the wall, while the focus of each parabola is a point 60 lying on a circle within the container wall. The liquid metal 12 flows into the inlet 62 of the sensing passage along the flow axis 58, and also in the general direction of the arrows 64, the rate at which the metal is drawn into the container interior being such that the flow is smooth and laminar and is directed in such flow to the central part 66, or throat, of the passage which is of minimum cross sectional flow area and constitutes the electric sensing zone proper. The molten metal discharges through the passage exit and is found in practice to be more of a jet flow, rather than following closely the part of the parabolic profile between the zone 66 and the outlet 68. The current I flows in the direction of the arrow 70 between the electrodes 20 and 28.

Figure 6:
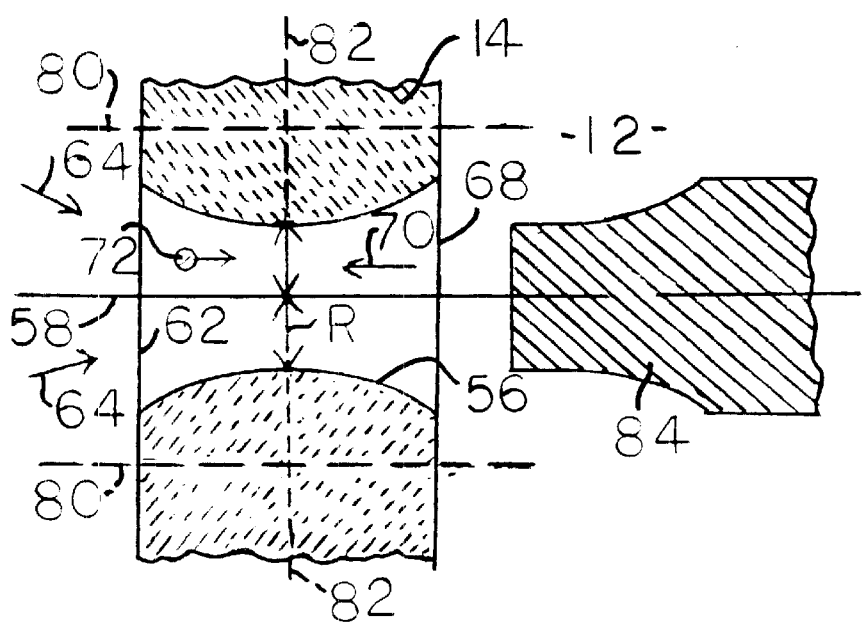
FIG. 6 shows to an enlarged scale a sensing passage in the side wall of a sampling tube wherein in accordance with the invention the sensing passage has an elliptic profile.

FIG. 6 also shows to an enlarged scale the portion of the wall of the sensing container 14 that includes the sensing passage 26 and, also in accordance with this invention, this has an elliptical profile with the major axis 80 parallel with the sensing passage longitudinal axis 58 and within the container wall and having an extension of its minor axis 82 passing through the electric sensing zone 66. As with the parabolic profile the elliptical profile is rotated about central longitudinal flow axis 58 to generate the wall 56 of the sensing passage.

The physical observation of the flow of molten metals is extremely difficult, since there are no transparent materials that can be used for making pipes through which the metals flow while under observation. The mathematical computation of the dynamic motion of particles in fluids also is notoriously difficult, and simplifying assumptions are essential; accordingly the treatment employed a two dimensional simulation using a cylindrical coordinate system. The computation domain was taken to be that between an inlet boundary 76 which is an inlet spherical cap centred at point C on the axis 58, this point being the intersection of axis 58 with a cone tangential to the passage wall 56 at the passage inlet edge; a corresponding outlet spherical cap 78 centred at point C' which is apex of a cone tangential to the passage wall at the passage outlet edge establishes the effective length of the sensing passage for computational purposes. It will be noted that in practice the transient time through the ESZ passage is not the time taken by a particle to go through the physical length of the passage, but rather the time it takes to go through the region where the pulse height generated is higher than the thresholds set by the electronic circuits for adequate detection and recognition. This computation length increases with particle size. The outlet boundary for the flow of the metal and the sensing current was taken to be the sensing passage throat 66. In addition, in order to simplify and enhance the accuracy of the calculations a non-orthogonal grid of variable spacing within the computational boundary was set up while time steps as small as $10^{-5}$ ms were employed.

At the inlet boundary 76 the liquid velocity and the electric current density were both assumed to be uniform and normal to the boundary, while at the outlet boundary 66 the electric potential was assumed to be constant and the exit velocity gradient zero; iterative corrections were made in any numerical calculations to match inflow and outflow rates so as to respect continuity. Jet flow of the molten metal was assumed beyond the throat 66, i.e. the diverging sidewalls at the outlet side were ignored and it was assumed that the liquid simply passes on with an axial velocity distribution of the same as that at the throat. Experiments with an aqueous system (which can be conducted at room temperature) showed that in practice a jet-type flow was obtained, and it seems safe to assume that the same will be true for the molten metal flow. The boundary conditions applied were zero slip along the passage wall and zero electric current flux across the tube between its inner and outer walls. The calculation was made assuming that the media is composed of one continuous material (the molten metal) of resistivity $P_e$ and sparsely distributed spherical inclusions of resistivity $P_{eff}$, the particles being considered as sufficiently scattered so that the distance between each other is large enough so as to not disturb the course of the surrounding current.

The LiMCA system usually is operated with molten aluminium while at a temperature of about 700° C., at which temperature its density is $2.368 \times 10^3$ kg/m$^3$, and its electrical resistivity ($\Omega$m) is $0.25 \times 10^{-6}$. The most common inclusions are alumina and gas micro-bubbles which have densities respectively of $3.8 \times 10^3$ kg/m$^3$ and zero, and which essentially are electrically non-conducting. Inclusions of titanium diboride were considered since its density is $4.5 \times 10^3$ kg/m$^3$, while its electrical resistivity is lower than that of alumina at $0.09 \times 10^{-6}$. It is found that the voltage pulse generated by a perfectly conducting particle is negative, opposite to that of a non-conducting particle, and has a peak resistive height two times that of a non-conducting particle of the same size, while aTiB$_2$ particle in molten aluminium also produces a voltage pulse of opposite sign because of its greater conductivity, the height of the voltage peak being about three fourths of that for a non-conductive particle of the same size.

Figure 7:
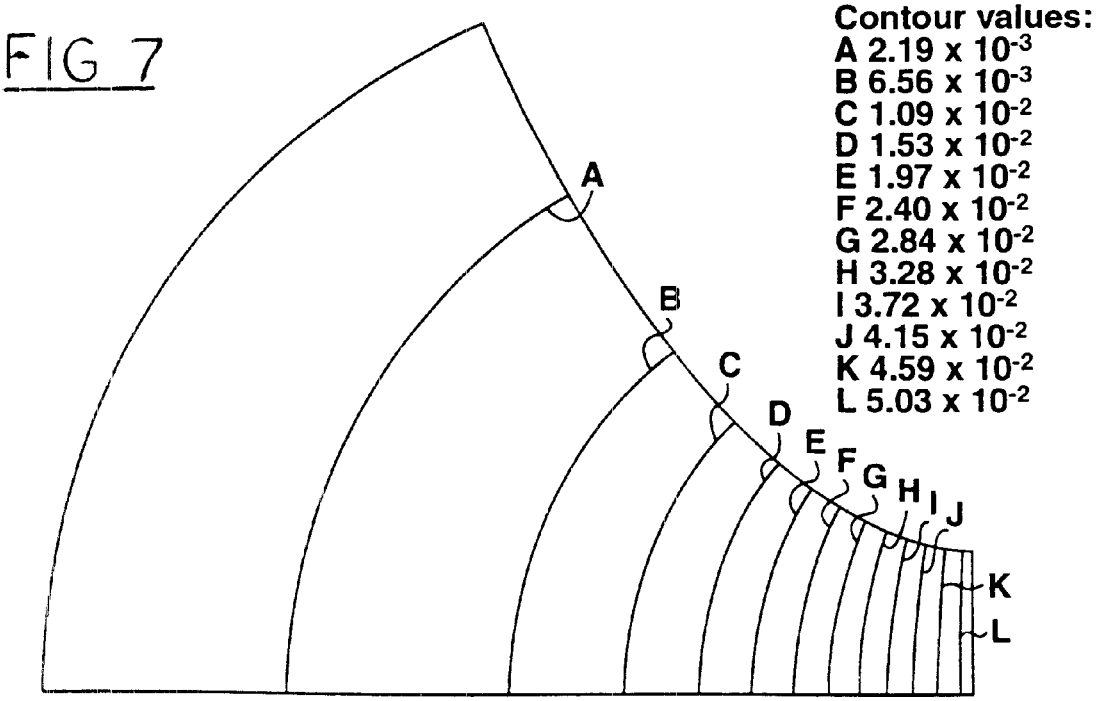
FIG. 7 is a plot of the electric potential distribution within the computation field.
Figure 8:
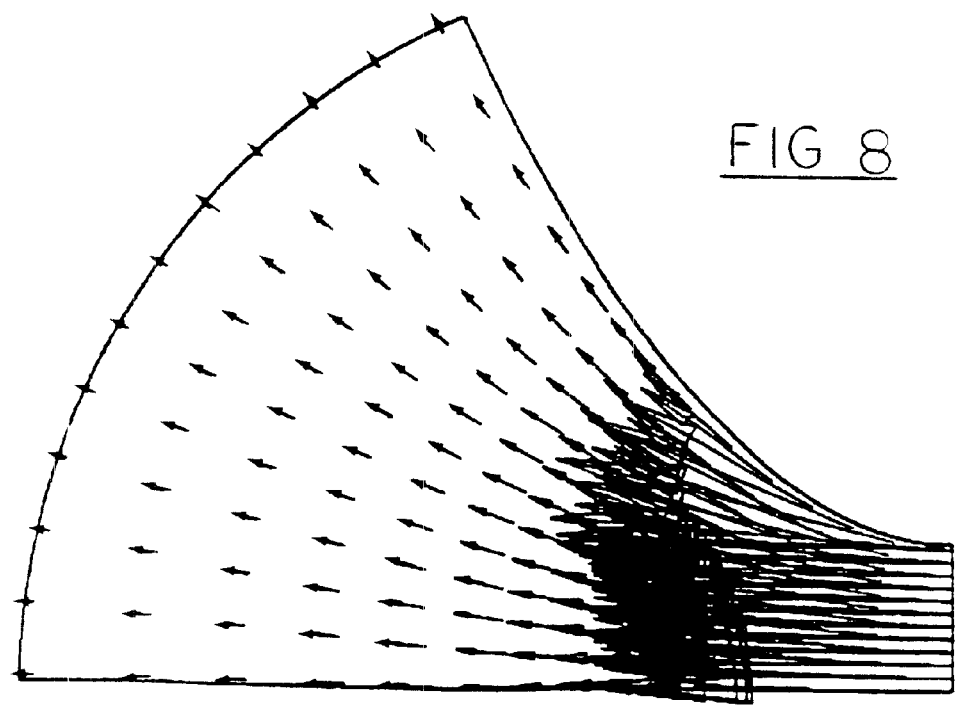
FIG. 8 is a plot of the electric current density within the field
Figure 9:
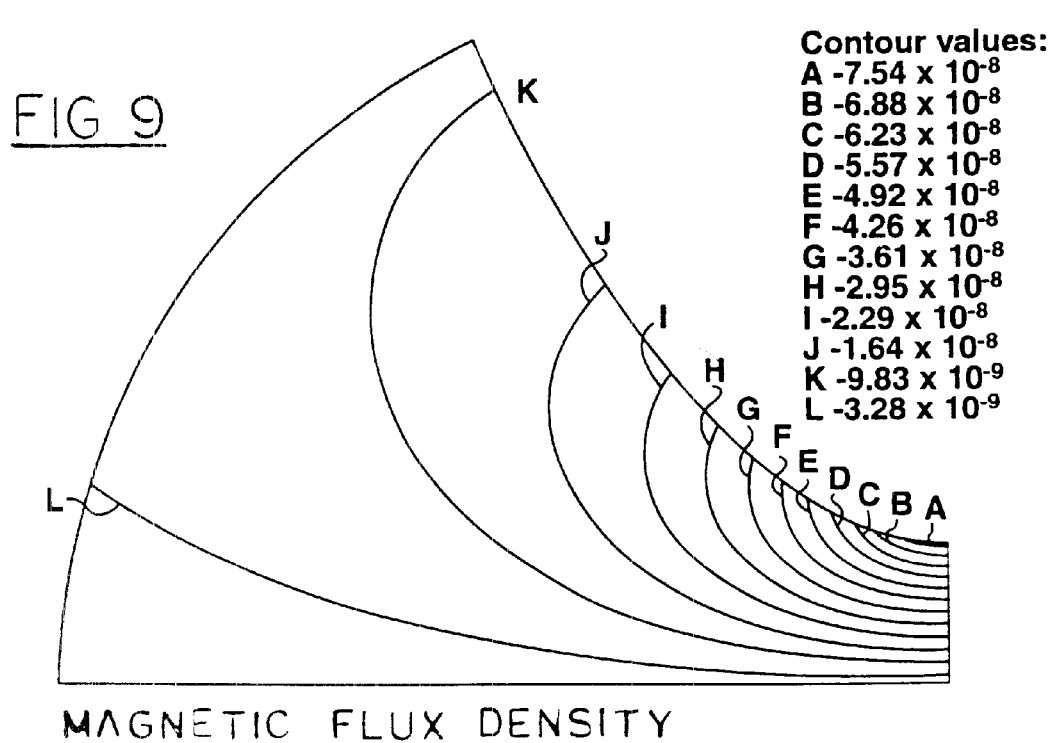
FIG. 9 is a plot of the self induced magnetic flux density within the field.
Figure 10:
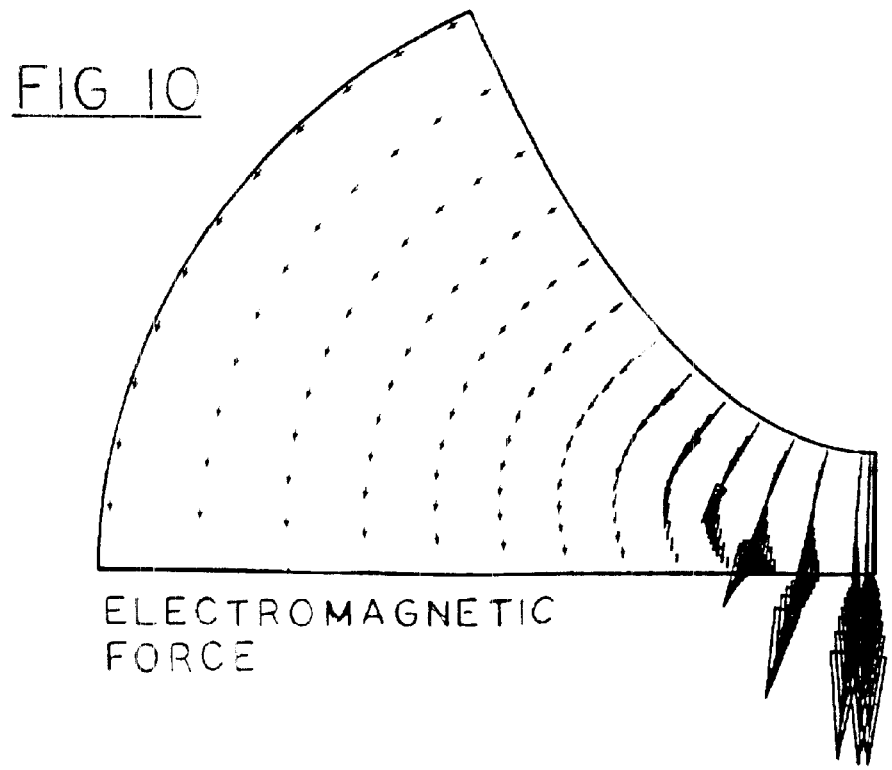
FIG. 10 is a plot of the specific electromagnetic force distribution within the field.

In order to predict the flow behaviour of molten aluminium entering the converging section of the sensing zone the metal was taken to be incompressible with constant properties, and the flow was considered lamina and steady, which are the ideal practical operating conditions. The metal flows at a speed of 4.6 m/s and the Reynolds number through the ESZ orifice is about 400, based on orifice diameter. The current generates a self-induced magnetic field with the result that all particles entrained in the moving metal are subjected to a corresponding electromagnetic field and resultant electromagnetic force. FIG. 7 shows the distribution of the electric potential within the computation field, FIG. 8 shows the electric current density, FIG. 9 shows the self-induced magnetic flux density, while FIG. 10 shows the specific electromagnetic force As can be seen from FIG. 7, which shows the calculated isopotential contours in the computational field and their respective values, the isopotential along the central cross section of the orifice has its highest value at contour L where the current flow from the inner positive electrode 22 enters the throat of the ESZ. The electrical potential gradient is very high near the throat of the orifice and drops gradually towards the entrance or exit of the orifice. With the usual measuring current of 60 amperes the voltage drop over the whole orifice is approximately 0.105 volts. This potential distribution gives rise to the electric current density distribution shown in FIG. 8 and therefore corresponds with it. Thus, as with the potential distribution the current density is very high near the central region of the orifice, and decreases with increasing distance from the throat. FIG. 9 shows the isodensity contours for the self-induced magnetic flux within the orifice and it will be seen that this increases from the central axis 58 to the passage wall 56. The interaction of this standard testing value electric current (60 amperes) and its induced magnetic flux results in an electromagnetic force whose distribution is shown in FIG 10.

Figure 11:
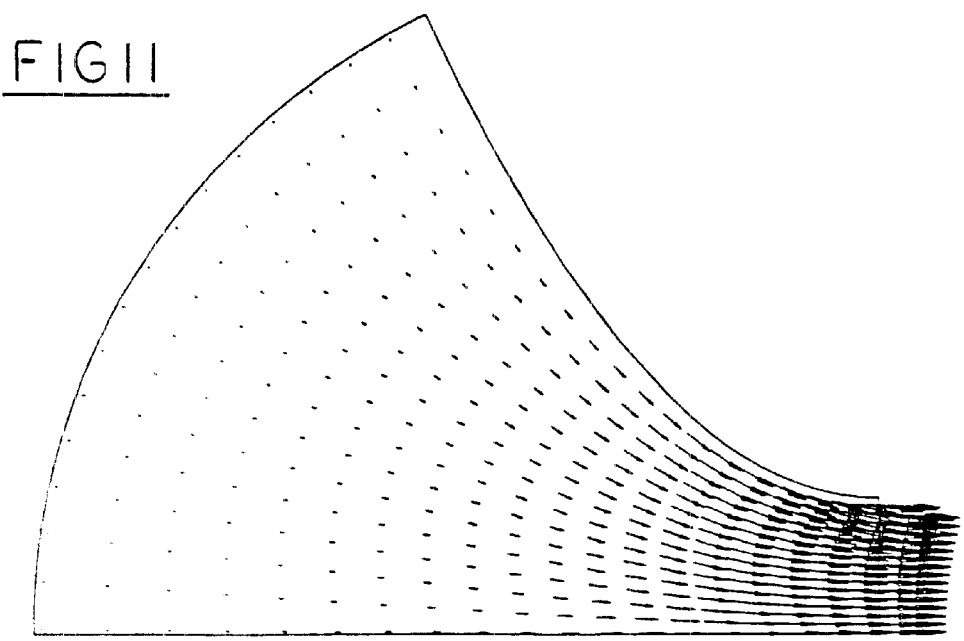
FIG. 11 is a plot of the computed metal flow vectors.
Figure 12:
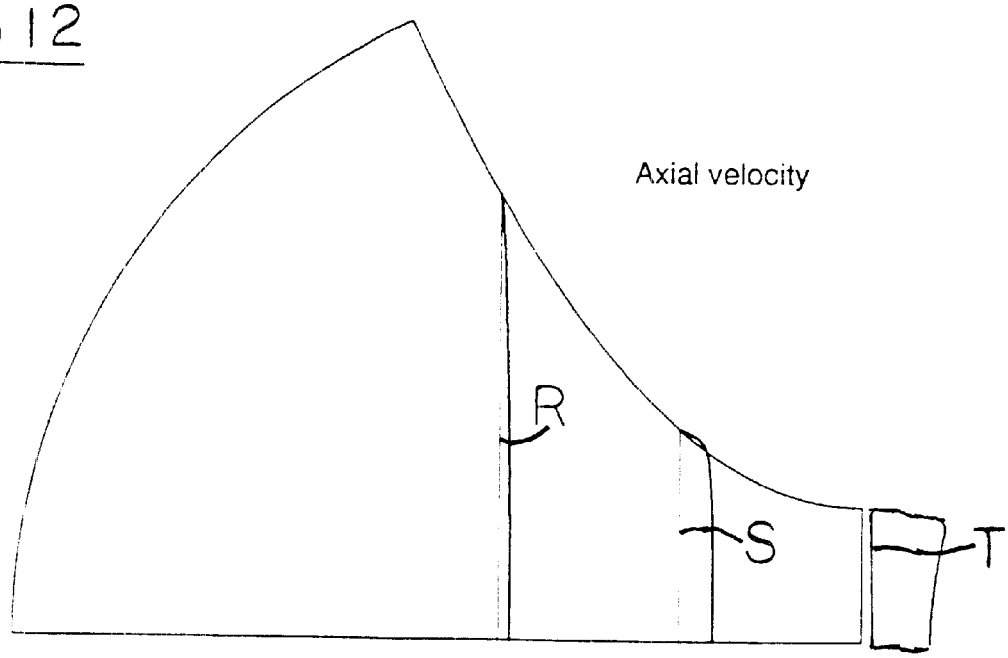
FIG. 12 shows the axial flow velocities at selected axially spaced points.
Figure 13:
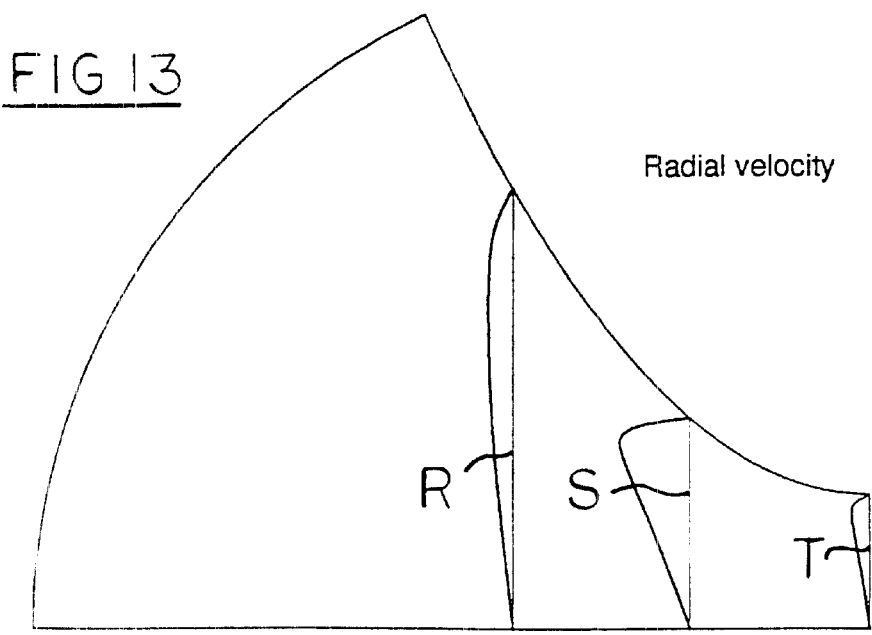
FIG. 13 shows the radial flow velocities at the same axially spaced points.
Figure 14:
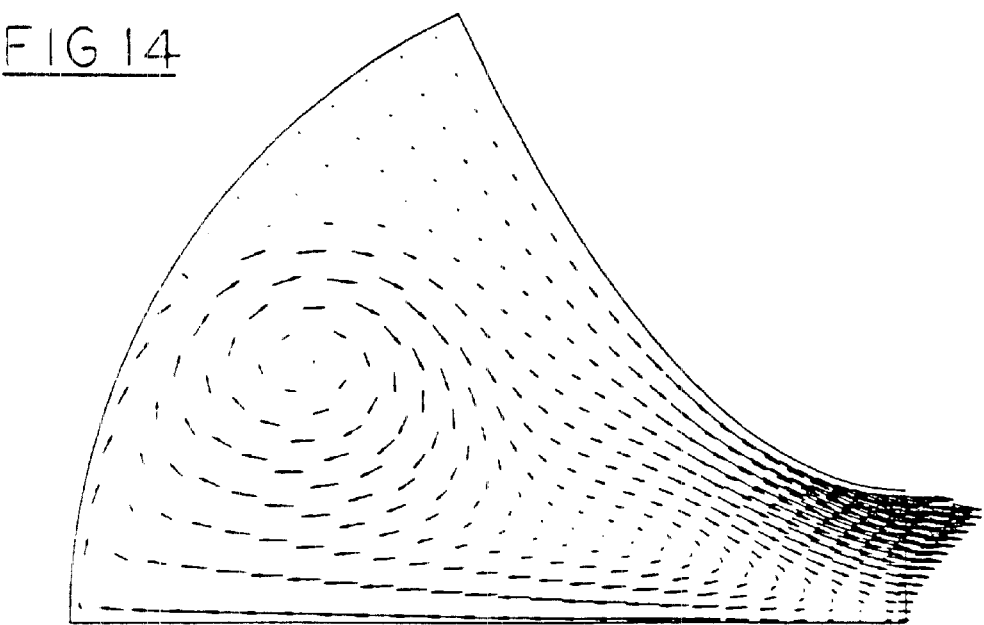
FIG. 14 shows the metal flow vectors when the current is above a threshold value resulting in a conditioning flow of the metal.

FIG. 11 shows the metal flow velocity vectors as computed, while FIG. 12 shows the profiles of the axial velocities at three selected axially spaced positions R, S and T in the sensing passage. FIG. 14 shows the equivalent profiles of the radial velocities at the same three selected axially spaced positions R, S and T. It can be seen that the stronger electric current density and magnetic flux density near the throat 66 of the orifice give rise to much stronger electromagnetic forces there than in the entrance or exit regions 62 and 68. The electromagnetic force is higher near the passage wall, but decreases toward the central axis 58, becoming virtually, and theoretically, zero along the central axis. In this force field particles suspended in molten aluminium that are electrically non-conductive experience an axial force in the opposite direction, urging them backwards against the metal stream, and a radial force that urges them toward the wall 56 out of the main flow of the molten metal. Particles that are electrically more conductive (e.g. $TiB_2$) than the aluminium experience an axial force in the same direction as the metal flow, and are pushed towards the central axis by the radially acting component of the force. With the current I at the usual measuring value the axial flow force produced by the vacuum source 38 is much higher than the opposed electromagnetic force, which is therefore relatively ineffective in opposing it. However, the radially acting forces are virtually unopposed and therefore are very effective.

The magnitude of these axial and radial electromagnetic forces are dependent directly on the value of the current I and increase therewith. Further computations, whose results are as shown in FIG. 14, show that at a threshold value of this current the increasing backwardly acting axial force, being increasingly stronger toward the passage throat, can reverse the metal flow and move the metal from the throat 66 to the entrance 62 with the result that a strong annular vortex flow is established in the entrance to the passage. The metal can now only flow into the sensing zone between the vortex and the wall and the velocity of the vortex flow is added to the metal flow at the passage wall; it has been found in practice that with a conditioning current of 250 amperes the maximum velocity at the wall increases from 4.64 m/s to at least 6.15 m/s. It seems reasonable therefore to ascribe the conditioning effect to this high fluid velocity near the wall, which is sufficiently high that it is able to scour away any debris or residual buildup of inclusions that have adhered to the wall entrain them in the vortex and then expel them back into the main metal stream.

The phenomenon is therefore a result of the magnetic pinch effect interacting with a precise shape of the entrance to the ESZ, the combination creating a pressure buildup in the orifice that at a critical current value causes a strong flow reversal at the entrance to the ESZ. There is therefore also a strong and definite advantage to the use of the precisely formed sensing passages of the invention in place of the randomly formed "smooth" rounded passages, or the cylindrical, or conical entrance passages proposed and used hitherto. As described above, at this time it is customary to use a conditioning current of 250–300 amperes in a LiMCA system intended for aluminium, since this is found to work under most circumstances. It can be shown however that with a parabola profile of a coefficient of 1.0, the lower end of the preferred range, the critical current value above which vortex flow is obtained is about 165 amperes, while the value is even lower for a profile of coefficient 5.0, which is at the upper end of the preferred range. It is possible therefore with these new profiles to operate with a battery system of lower capacity when these lower conditioning currents are able to establish a conditioning vortex flow.

Another general problem encountered with the measurements made in flowing liquid metals is the tendency as described for particles to be repelled radially outward and also to some extent axially backwards along the flow axis. It is known that this does reduce the total number of particles that pass through the sensing zone during a standard test, as can be determined testing the same melt by the slower and more expensive, but more comprehensive prior art methods employed before the LIMCA system became available. The proportion that passes through is known as the pass-through fraction and if the operating parameters are not sufficiently carefully chosen it can be as low as 50%. Since the rejection of the particles clearly is due to the random motions of the particles under the action of the electromagnetic force as the metal stream passes through a rough walled sensing passage of indeterminate or unsuitable profile, then the adoption of the progressive parabolic or elliptical profiles of the invention, together with the adoption of the much smoother machining proposed for the passage wall, will result in a substantial decrease in the fraction that is rejected. For example, if a non-conductive particle is considered to be collected by the passage wall when it assumes a radial velocity toward the central axis 58, and its centre is a radius away from the wall, then the calculated collection coefficient for particles of size 20–240 μmn is only 5% in a parabolic profile passage with a polynomial coefficient of 2.15, and is still only 8% when the polynomial coefficient is 1.0.

A problem encountered with the application of the system to the analysis of magnesium is to find a material for the tube 14 that is resistant to attack by the molten metal. The physical properties of liquid magnesium are not very much different from those of aluminium, with a liquid temperature of 700° C., a density of $1.577 \times 10^{-3}$ kg/m$^3$, a viscosity of $1.23 \times 10^{-3}$ kg/ms and an electrical resistivity of $0.28 \times 10^{-6}$. Compacted silica tubes are resistant to such attack but tend to crack easily due to thermal shock and had a high failure rate. A more recent proposal is to form the sensing passage in a disc of boron nitride which is then held between two steel tubes that support the disc with the inner one forming the sampling chamber. In neither of these constructions is it possible to smooth the entrance by a heating procedure, as with aluminium, and instead the passage has been formed with a cylindrical bore at the ESZ throat and conical openings at the entrance and exit. It was found that the background noise encountered is significantly higher than the value of about 10 $\mu$V obtained with aluminium, namely usually about 30–50 $\mu$V, and the sensing orifice size required is also significantly larger to avoid blockage, namely about 400–500 $\mu$m, both of which increase the minimum size of particle that can be reliably detected. It is found by computation that even at the standard operating current for aluminium of 60 amperes a large toroidal vortex or recirculation zone is established inside the conical entrance, again generated by the strong electromagnetic pinch force at the passage entry and the consequent strong axial backpressure it produces. Such a vortex would itself cause an increase in background noise, such as is encountered. It is also believed that it may be an explanation for the requirement for a larger passage in that particles are entrained in the vortex and cannot reach the sensing zone throat. Instead they are swept around in the vortex giving them an opportunity to coalesce and become larger particles that more easily block the passage, or if able to pass through the passage are then counted as such, giving an inaccurate count. It will be seen that the provision of an accurately formed passage of the profiles of the invention and of the surface smoothness specified will be able to raise the current flow at which vortex formation takes place above the value of 60 amperes, which is needed for accurate and reliable testing, while also making it possible to predict the higher current value at which a vortex of sufficient axial velocity will form for adequate conditioning as and when required.

Steel is another metal for which fast and reliable inclusion detection is required since many characteristics of a steel product can be badly compromised by the presence of inclusions, such as ductility, toughness, drawability, machinability, weldability, H.I.C, and fatigue strength, as well as surface characteristics such as paintability, pitting, corrosion and reflectivity, all of which can be critically affected by the nature, size and spatial density of such inclusions. Current methods employed are relatively time consuming and costly and inherently cannot be operated on-line. Depending on the grades of the steel being produced, and attendant processing operations, large inclusions, typically in the range of 50–200 $\mu$m diameter can be present. Since the successful application of the YMCA system to aluminium melts much effort has been devoted to the development of sensor probes for liquid steel. An initial design employed a composite boron-nitride/Silica (fused quartz) tube that is usable as long as the steel is properly deoxidized beforehand. The part of the tube of boron nitride was immersed in the melt and remained chemically stable therein while the quartz upper body was above the melt and provided the visibility needed to control successive filling and emptying operations. This design was found to be prone to leaks at the boron nitride/silica joint, and consequently was abandoned In favor of a one-piece silica tube supported by a graphite reinforcing inner electrode and using a cylindrical ESZ. Although it has been successful sometimes the operations are troubled by the relatively high background noise, and furthermore, it is observed that the high background noise cannot always be improved by conditioning. The pertinent properties of liquid silicon-boron steel are melt temperature 1350° C., a density of $7.0 \times 10^{-3}$ kg/m$^3$, a viscosity of $7.0 \times 10^{-3}$ kg/ms and an electrical resistivity of $1.40 \times 10^{-6}$.

The velocity vectors for flow of liquid steel within the ESZ were examined with an operating current of 20 Amperes, and a conditioning current of 200 Amperes, the adoption of lower current values than those for aluminium being indicated by the much higher resistivity of the steel. It was found that the maximum velocities are along the central axis for both cases, but surprisingly the maximum velocity is lower in the conditioning operation than that in a typical testing operation. This is in contrast to the conditioning effect in molten aluminum, where the recirculation zone formed in the inlet region with an increased current dramatically increases the fluid velocity near the ESZ wall. It can be inferred that the ineffective conditioning operation in steel with the higher current is the direct result of the cylindrical shape of the ESZ and use of a sensing passage of either a parabolic or elliptical profile of the invention, together with the adoption of the preferred highly smoothed wall surface for the passage, would remove this anomaly and result in an overall operation similar to those obtained with aluminium and magnesium. Calculations for steel employing a parabolic profile passage of 2.15 coefficient gave a threshold current value of 184 amperes at 4 m/s and 86 amperes at 2 m/s, as compared with equivalent values for aluminium of 110 and 58 amperes respectively, showing that with the correct design of passage the critical current value for steel is higher, as should be expected.

A major advantage of the use of sensing passages of precisely formed profile and surface smoothness is the ability to determine and adjust the values of the sensing and conditioning currents to be employed for a procedure. Thus, it is essential for accurate measurement that the testing current be sufficiently high without producing disruption of laminar flow, and conversely that the conditioning current does produce the required strong vortex flow. The threshold current value at which vortex flow is produced also depends upon other parameters, such as the flow rate of the metal and the diameter of the passage throat, both of which are inter-related. The choice of passage diameter has been described above. The choice of flow rate is dictated by the need for a large enough sample flowing into the sample chamber to give meaningful results, without the test taking an unduly long period of time as the metal flows into the chamber. Owing to the small passage diameters involved the flow rate must be relatively large, and usually is in the range 2–4 m/s. Since the transition from laminar to turbulent flow is dependent upon the current at which the electromagnetic force overcomes the flow rate the threshold value is also dependent on the flow rate.

The following Table shows examples of this interdependence of the value of the threshold current I for parabolic profile sensing passages of 300 $\mu$m diameter, 1 mm length and of polynomial value A from 0.1 to 10, the metal being aluminium. It will be noted that the value decreases progressively until it becomes impractically low at the highest values:

| Value A | Flow 4 m/s | Flow 3 m/s | Flow 2 m/s |
| --- | --- | --- | --- |
| 0.1 | 450 amps | 340 amps | 231 amps |
| 1.0 | 165 amps | 126 amps | 87 amps |
| 2.15 | 110 amps | 84 amps | 58 amps |
| 3.8 | 70 amps | 54 amps | 38 amps |
| 10.0 | 11 amps | | |

An equivalent table for an elliptical profile passage gives the following results:

| λ Value | Flow 4 m/s |
| --- | --- |
| 0.2 | 370 amps |
| 0.5 | 175 amps |
| 1.0 | 140 amps |
| 2.0 | 47 amps |

We claim:

1. A molten metal inclusion sensor probe which is immersed in the molten metal and detects inclusions therein by the electric sensing zone method employing a lower value measuring current and a higher value conditioning current, the probe comprising a sensor probe body of electrically insulating heat resistant material having in at least a part of a wall thereof a sensing passage for the flow of molten metal from one side of the body to the other, the sensing passage providing therein an electric sensing zone and extending about a longitudinal axis;

wherein the sensing passage decreases progressively in flow cross section area from its entrance to the electric sensing zone;

wherein the profile of the sensing passage from its entrance to the electric sensing zone is selected from a parabola having the parabola determinant coincident with the sensing passage longitudinal axis and the focus within the sensor probe body and spaced from the sensing passage, the parabola employing a coefficient in the range 1.0 to 5.0, and a segment of an ellipse having one axis parallel with the sensing passage longitudinal axis and within the body and having an extension of its other axis passing through the electric sensing zone, the ellipse employing a coefficient in the range 0.2 to 2.5; and wherein the sensing passage has been produced by an operation to have a wall surface smoothness at least from its entrance and through the electric sensing zone of better than 1.016 micrometers (40 microinches);

whereby smooth laminar fluid flow through the electric sensing zone is obtainable upon the application of predetermined values of measuring current thereto, and vortex conditioning fluid flow is obtainable at the sensing passage entrance upon application of corresponding predetermined values of conditioning current thereto.

2. A sensor probe as claimed in claim 1, wherein the profile of the sensing passage from the electric sensing zone to its exit is also selected from, a parabola having the parabola determinant coincident with the sensing passage longitudinal axis and the focus within the sensor probe body end spaced from the sensing passage, the parabola employing a coefficient in the range 1.0 to 5.0, and a segment of an ellipse having one axis parallel with the sensing passage longitudinal axis and within the body and having an extension of its other axis passing through the electric sensing zone, the ellipse employing a coefficient in the range 0.2 to 2.5.

3. A sensor probe as claimed in claim 1, wherein when the sensing passage from its entrance and through the electric sensing zone is of parabolic profile it employs a parabola of coefficient within the range 2.0 to 4.0, and when it is of elliptic profile it employs a segment of an ellipse of coefficient within the range 0.5 to 2.0.

4. A sensor probe as claimed in claim 2, wherein when the sensing passage from the sensing zone to its exit is of parabolic profile it employs a parabola of coefficient within the range 2.0 to 4.0, and when it is of elliptic profile it employs a segment of an ellipse of coefficient within the range 0.5 to 2.0.

5. A sensor probe as claimed in claim 1, wherein the sensing passage has been produced by the operation to have a wall surface smoothness of better than 0.264 micrometers (10 microinches).

6. A sensor probe as claimed in claim 5, wherein the sensing passage has been produced by the operation to have a wall surface smoothness of better than 0.127 micrometers (6 microinches).

7. A method of making a molten metal inclusion sensor probe which is immersed in the molten metal and detects inclusions therein by the electric sensing zone method employing a lower value measuring current and a higher value conditioning current, the probe comprising a sensor probe body of electrically insulating heat resistant material having in at least a part of a wall thereof a sensing passage for the flow of molten metal from one side of the body to the other, the sensing passage providing therein an electric sensing zone and extending about a longitudinal axis;

the method including the step of forming the sensing passage in the wall by a machining operation whereby from at least the entrance and through the electric sensing zone the wall surface is of smoothness better than 1.016 micrometers (40 microinches);

wherein the sensing passage thus formed decreases progressively in flow cross section area from its entrance to the electric sensing zone; and wherein the profile of the sensing passage from its entrance to the electric sensing zone is selected from a parabola having the parabola determinant coincident with the sensing passage longitudinal axis and the focus within the sensor probe body and spaced from the sensing passage, the parabola employing a coefficient in the range 1.0 to 5.0, and a segment of an ellipse having one axis parallel with the sensing passage longitudinal axis and within the body and having an extension of its other axis passing through the electric sensing zone, the ellipse employing a coefficient in the range 0.2 to 2.5;

whereby smooth laminar fluid flow through the electric sensing zone is obtainable upon the application of predetermined values of measuring current thereto, and vortex conditioning fluid flow is obtainable at the sensing passage entrance upon application of corresponding predetermined values of conditioning current thereto.

8. A method as claimed in claim 7, wherein the profile of the passage from the electric sensing zone to its exit is also selected from a parabola having the parabola determinant coincident with the sensing passage longitudinal axis and the focus within the sensor probe body and spaced from the sensing passage, the parabola employing a coefficient in the range 1.0 to 5.0, and a segment of an ellipse having one axis parallel with the sensing passage longitudinal axis and within the body and having an extension of its other axis passing through the electric sensing zone, the ellipse employing a coefficient in the range 0.2 to 2.5.

9. A method as claimed in claim 7, wherein when the passage from its entrance and through the electric sensing zone is of parabolic profile it employs a parabola of coefficient within the range 2.0 to 4.0, and when it is of elliptic profile it employs a segment of an ellipse of coefficient within the range 0.5 to 2.0.

10. A method as claimed in claim 8, wherein when the passage from the electric sensing zone and through its exit is of parabolic profile it employs a parabola of coefficient within the range 2.0 to 4.0, and when it is of elliptic profile it employs a segment of an ellipse of coefficient within the range 0.5 to 2.0.

11. A method as claimed in claim 7, wherein the sensing passage has been produced to have a wall surface smoothness of better than 0.254 micrometers (10 microinches).

12. A method as claimed in claim 11, wherein the sensing passage has been produced to have a wall surface smoothness of better than 0.127 micrometers (5 microinches).

13. A molten metal inclusion sensor probe which is immersed in the molten metal and detects inclusions therein by the electric sensing zone method employing a lower value measuring current and a higher value conditioning current, the probe comprising a sensor probe body of electrically insulating heat resistant material having in at least a part of a wall thereof a sensing passage for the flow of molten metal from one side of the body to the other, the sensing passage providing therein an electric sensing zone and extending about a longitudinal axis;

wherein the sensing passage decreases continuously smoothly and progressively in flow cross section area from its entrance to the electric sensing zone and increases continuously smoothly and progressively from the electric sensing zone to its outlet; and wherein the sensing passage has been produced by a machining operation to be symmetric about a longitudinal axis in the direction of flow through the sensing passage and to have a wall surface smoothness of better than 1.016 micrometers (40 microinches);

whereby smooth laminar fluid flow through the sensing passage is obtainable upon the application of predetermined values of measuring current thereto, and vortex conditioning fluid flow is obtainable at the entrance to the sensing passage upon application of corresponding predetermined values of conditioning current thereto.

14. A sensor probe as claimed in claim 13, wherein the sensing passage has a wall surface smoothness of better than 0.254 micrometers (10 microinches).

15. A sensor probe as claimed in claim 14, wherein the sensing passage has a wall surface smoothness of better than 0.127 micrometers (5 microinches).

16. A method of making a molten metal inclusion sensor probe which is immersed in the molten metal and detects inclusions therein by the electric sensing zone method employing a lower value measuring current and a higher value conditioning current, the probe comprising a sensor probe body of electrically insulating heat resistant material having in at least a part of a wall thereof a sensing passage for the flow of molten metal from one side of the body to the other, the sensing passage providing therein an electric sensing zone and extending about a longitudinal axis;

the method including the step of forming the sensing passage in the wall by a machining operation to be symmetric about its longitudinal axis, to have a continuously smoothly and progressively decreasing flow cross section area from its entrance to the electric sensing zone and to have a continuously smoothly and progressively increasing flow cross section area from the sensing zone to its outlet; and wherein the machining operation produces a wall surface smoothness through the sensing passage of better than 1.016 micrometers (40 microinches);

whereby smooth laminar fluid flow through the sensing passage is obtainable upon the application of predetermined values of measuring current thereto, and vortex conditioning fluid flow is obtainable at the entrance to the sensing passage upon application of corresponding predetermined values of conditioning current thereto.

17. A method as claimed in claim 16, wherein the sensing passage has a wall surface smoothness of better than 0.254 micrometers (10 microinches).

18. A method as claimed in claim 17, wherein the sensing passage has a wall surface smoothness of better than 0.127 micrometers (5 microinches).

* * * * *